United States Patent
Miau et al.

(10) Patent No.: US 8,057,236 B2
(45) Date of Patent: Nov. 15, 2011

(54) PHANTOM AND ITS MANUFACTURING METHOD

(75) Inventors: Luo-Hwa Miau, Taipei County (TW); Chang-Lin Hu, Kaohsiung (TW); Tung-Ming Yu, Yilan County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 463 days.

(21) Appl. No.: 12/401,223

(22) Filed: Mar. 10, 2009

(65) Prior Publication Data

US 2010/0112538 A1    May 6, 2010

(30) Foreign Application Priority Data

Oct. 31, 2008    (TW) ................................ 97142119 A

(51) Int. Cl.
*G09B 23/28* (2006.01)
(52) U.S. Cl. ........................................................ 434/267
(58) Field of Classification Search .................. 434/262, 434/267, 268, 272, 273, 275, 296
See application file for complete search history.

(56) References Cited

U.S. PATENT DOCUMENTS

| | | | | |
|---|---|---|---|---|
| 4,134,218 A | * | 1/1979 | Adams et al. | 434/267 |
| 4,493,653 A | * | 1/1985 | Robbins et al. | 434/262 |
| 4,974,461 A | * | 12/1990 | Smith et al. | 73/865.6 |
| 5,055,051 A | * | 10/1991 | Duncan | 434/262 |
| 5,518,406 A | * | 5/1996 | Waters | 434/267 |
| 5,850,033 A | * | 12/1998 | Mirzeabasov et al. | 73/12.01 |
| 6,083,008 A | * | 7/2000 | Yamada et al. | 434/267 |
| 7,058,168 B1 | * | 6/2006 | Knappe et al. | 379/204.01 |
| 7,419,376 B2 | * | 9/2008 | Sarvazyan et al. | 434/273 |
| 7,575,434 B2 | * | 8/2009 | Palakodeti | 434/267 |
| 2006/0184005 A1 | | 8/2006 | Sakezles | |
| 2009/0098521 A1 | * | 4/2009 | Kuo et al. | 434/267 |

FOREIGN PATENT DOCUMENTS

DE    29520960 U1    6/1996
GB    2416909 A    2/2006

* cited by examiner

*Primary Examiner* — Kurt Fernstrom
(74) *Attorney, Agent, or Firm* — Morris Manning Martin LLP; Tim Tingkang Xia, Esq.

(57) ABSTRACT

A phantom manufacturing method is disclosed, which comprises the steps of: disposing an exudate network with interconnecting first channel and second channel in a container in a manner that the first channel is transversely disposed for an exudate to flow laterally in the container and the top portion of the second channel is longitudinally disposed for the exudate to flow vertically in the container; forming a plurality of stacking solid layers while arranging the first channel at the bottommost solid layer and the top of the second channel at either inside the topmost solid layer or to be exposed outside the top of the topmost solid layer as the bottom of the second channel is connected to the first channel and extending therefrom upward to the topmost solid layer; and forming a recess in the topmost solid layer while connecting the bottom thereof to the second channel.

18 Claims, 4 Drawing Sheets

| | Actual wound experiment | Phantom experiment |
|---|---|---|
| Nagative pressure | -125mmHg | -125mmHg |
| Wound pressure | -123mmHg | -121mmHg |
| Wound size(diameter) | 30mm | 30mm |
| Dressing | PU | PU |
| Required time for reaching the specific nagative pressure | 10 seconds | 8 seconds |

PHANTOM AND ITS MANUFACTURING METHOD

FIELD OF THE INVENTION

The present invention relates to a phantom and the manufacturing method thereof, and more particularly, to a phantom having an exudate network connecting to a sculpted opening simulating a wound to be used for experimenting how exudates can affect the efficiency of a negative pressure wound therapy (NPWT) system.

BACKGROUND OF THE INVENTION

Generally, a vacuum assisted closure (VAC) therapy or a negative pressure wound therapy (NPWT), being classified as a kind of adjuvant physical therapy, is operated by applying a negative pressure pump to a patch of a bio-compatible porous wound dressing covering a wound for forming a negative pressure inside the wound, by that, as the negative pressure will cause the volume of the porous wound dressing to contract and consequently force the wound to close as well as the shear stresses of the contracted porous wound dressing will cause a drag to the boundary tissues of the wound for enhancing cell division and proliferation, the healing of the wound can be accelerated. It is noted that the application of the negative pressure through the porous wound dressing not only can improve the growth of blood vessels and the local blood circulation as the flowing of tissue fluid between cells can be enhanced, but also it can prevent the happening of edema and inflammation, create a moist healing environment with good wound protection as it can draw cellular waste and excess tissue fluid out of the wound, and thus the healing time of the wound can be reduced.

Conventionally, the development of a NPWT system must go through several clinical experiments just to verify its effectiveness in physical and biological therapy. Currently, it is common to use living animal, such as pig, rabbit or mouse, in such clinical experiments. However, not to mention the difficulties in development of a NPWT system using the result of such animal experiment as there are conceivable differences between human tissue and animal tissue, just the more and more strict animal experiment regulation by the effort of humanitarian and animal protection associations will cause huge delay in developing a mature NPWT product.

In view of the aforesaid shortcomings, there are already many phantoms that are capable of mimicking human tissue being developed for using in those therapeutic effectiveness verifications, such as solid water phantom, polystyrene phantom acrylic phantom, thermoplastic phantom and gelatin phantom, etc. The aforesaid phantoms are mostly being molded into blocks or other geometrical shapes so as to facilitate the proceeding the effectiveness verifications. It is noted that the gelatin phantom made of animal protein can be applied in applications more than those other phantoms. In food industry, it can be made into all kinds of soft sweets, mousse, jelly, meat aspic, cakes, and so on; and in pharmaceutical industry, it can be made into hard capsules, soft capsules, sugar-coated pills, and so on; and in biomedicine industry, it can be made into artificial dressings, artificial skins and phantoms, and so on. As the gelatin can form a smooth and elastic jelly that its strength is adjustable according to its gelatin concentration, and is a hydrophile jelly capable of melting into liquid-like glue when it is heated to a temperature above 40° C. and solidifying back into jelly when it is cooled down to below 30° C., phantoms of different elasticity and thicknesses can be made from gelatins of different compositions for the purpose of mimicking different layers in a human skin like epidermis layer, dermis layer, and subcutaneous layer. Moreover, the gelatin phantom can be formed with a plurality of layers, each having channels formed therein to be used for operating as the blood vessels in the skin as there can be a blood mimicking fluid flowing in those channels.

However, as the channels of different layers in the conventional gelatin phantom are not formed interconnecting with each other, the blood mimicking fluid is prohibited from flowing between layers so that even the blood mimicking fluid flowing in the channels of the topmost layer is flowing under a sculpted wound formed on the gelatin phantom and can not ooze out of the wound just likes an actual skin wound does. It is known that the human blood and tissue fluid are capable of flowing between skin layers and thus it is for sure that there will be blood and tissue fluid ooze out of an open wound at any time during the healing. Therefore, the conventional gelatin phantom can not mimic the exudate of an open wound, there will be errors when it is used for experimenting how exudates can affect the efficiency of a negative pressure wound therapy (NPWT) system.

SUMMARY OF THE INVENTION

In view of the disadvantages of prior art, the object of the present invention is to provide a phantom and its manufacturing method, in which the phantom is configured with an exudate network connecting to a sculpted opening simulating a wound to be used for experimenting with high accuracy how exudates can affect the efficiency of a negative pressure wound therapy (NPWT) system.

To achieve the above object, the present invention provides a method for manufacturing a phantom, which comprises the steps of: disposing an exudate network with interconnecting at least a first channel and at least a second channel in a container in a manner that the first channel is transversely disposed for an exudate to flow laterally in the container and the top portion of the second channel is longitudinally disposed for the exudate to flow vertically in the container; forming a plurality of solid layers by stacking one on top of another while enabling the first channel to be disposed at the bottommost solid layer and the top of the second channel to be disposed either inside the topmost solid layer or exposed outside the top of the topmost solid layer as the bottom of the second channel is connected to the first channel and extending therefrom upward to the topmost solid layer; and forming a recess in the topmost solid layer in a manner that the bottom of the recess is connected to the second channel.

Moreover, the present invention provide a phantom, which comprises: a plurality of solid layers, formed by stacking one on top of another while enabling a second solid layer to be disposed on top of a first solid layer in the plural solid layers; and at least an exudate network, formed inside the plural solid layers with interconnecting at least one first channel and at least one second channel in a manner that the at least one first channel is transversely disposed for an exudate to flow laterally in the first solid layer and the at least one second channel is longitudinally disposed for the exudate to flow vertically; wherein, the top of the second channel is disposed either at the top of the second solid layer or exposed outside the second solid layer as the bottom of the second channel is connected to the first channel and extending therefrom upward to the topmost solid layer.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
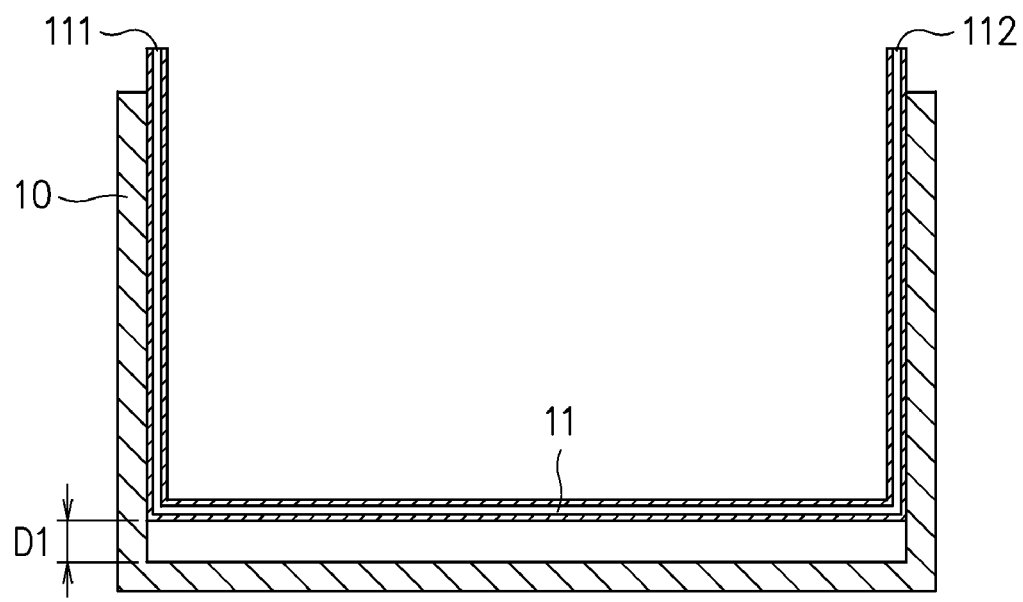
FIG. 1 to FIG. 4 are schematic diagrams showing steps of a method for manufacturing a phantom according to the present invention.

Please refer to FIG. 1 to FIG. 4, which are schematic diagrams showing steps of a method for manufacturing a phantom according to the present invention. In FIG. 1, the phantom formation process starts by disposing a first channel 11 of an exudate network in a container 10 while enabling the first channel 11 to be transversely disposed for an exudate to flow laterally in the container 10. As the cross sectional view shown in FIG. 1, the first channel 11 is a tube-like structure being configured with an inlet 111 and an outlet 112 in a manner that the inlet 111 is provided for the exudate to flow into the first channel 11 while the outlet 112 is provided for the exudate to flow out of the first channel 11. As the first channel 11 is configured with the inlet 111 and the outlet 112 for the exudate to flow in and out of the same, it is able to simulate the circulation of blood or tissue fluid in human body. In FIG. 1, the first channel 11 and the inner bottom of the container 10 is spaced by a distance D1, that is realized by the support of certain supporting devices such as strut. The supporting devices that can be used for supporting and elevating the first channel 11 by a distance D1 is known to those skilled in the art and thus will not be described further herein. As for the function for designing the distance D1 between the first channel 11 and the inner bottom of the container 10 will be described hereinafter.

Figure 2:
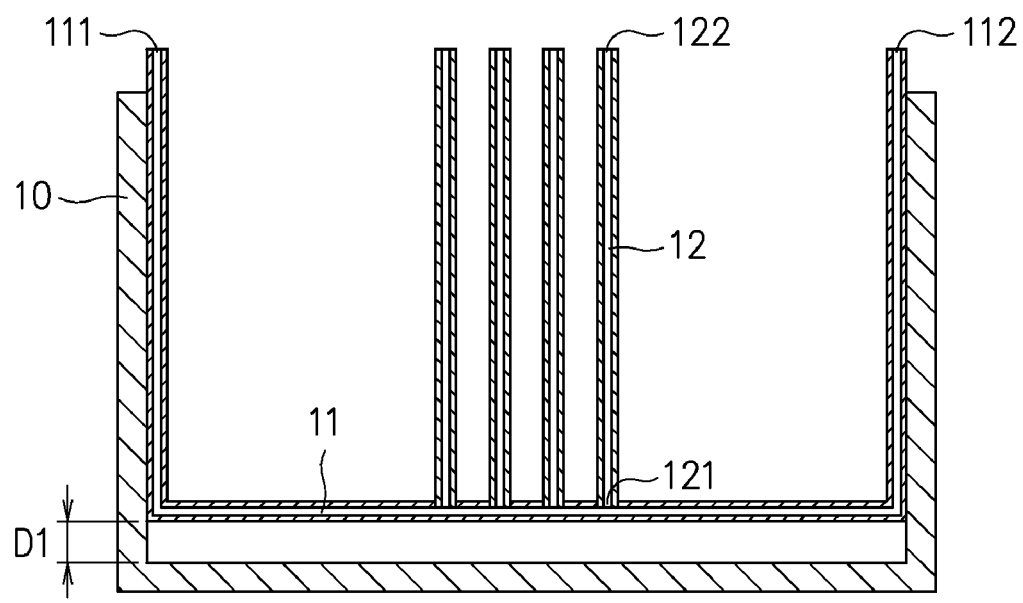

In FIG. 2, there is a plurality of second channels 12 formed in the middle section of the first channel 11, and each of the plural second channel 12 is a narrow straight tube-like structure being formed in a manner that the bottom 121 of each second channel 12 is connected to the first channel 11 and the top 122 thereof is extending vertically upward by a length. It is noted that a supporting device such as struts is used for maintaining uprightness and position of each second channel 12.

Figure 3:
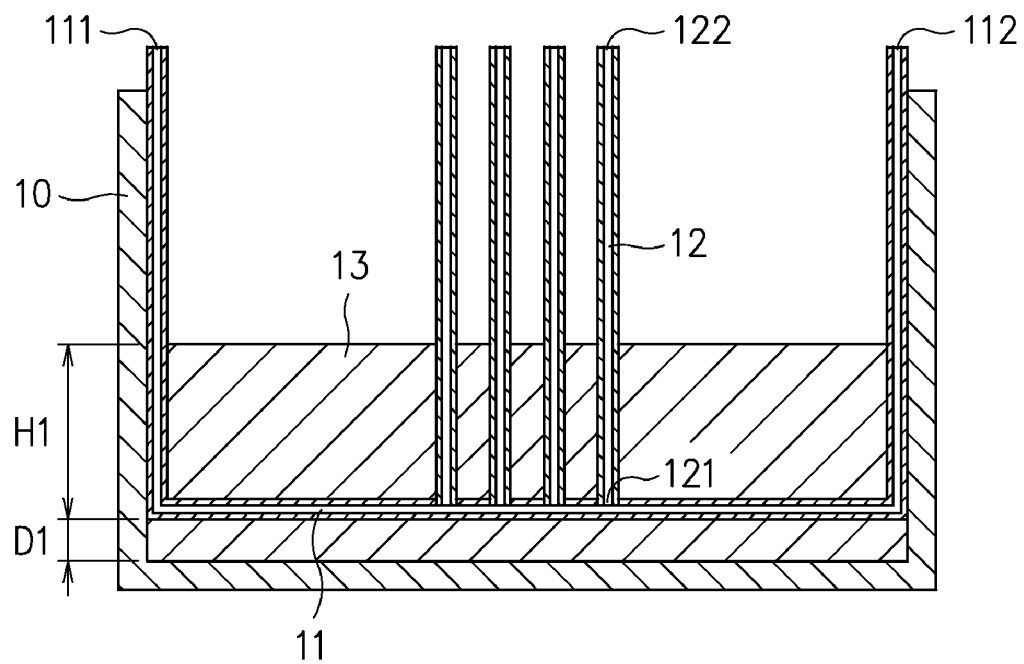

As shown in FIG. 3, a melted raw material for forming the phantom is fed into the container 10 up to an extent that a height H1 is reached and thus the first channel 11 is submerged under the raw material while leaving the top 122 of each second channel 12 exposed. After allowing the container 10 to stand for a period of time, the melted raw material of the height H1 is cooled down and thus solidified into a first solid layer 13. It is noted that the melted raw material for forming the phantom is a material selected from the group consisting of various mixtures of gelatin and water in different proportions. Moreover, during the period of time when the container is allowed to stand for the first solid layer 13 to solidify, a cooling device such as a fridge or a low-temperature storage cabinet can be used for assisting the melted raw material to cool down and thus solidify into the first solid layer 13. That is, the container 10 can be put into the cooling device for a period of time, e.g. 30 minutes, so as to assist the solidification of the first solid layer 13.

Figure 4:
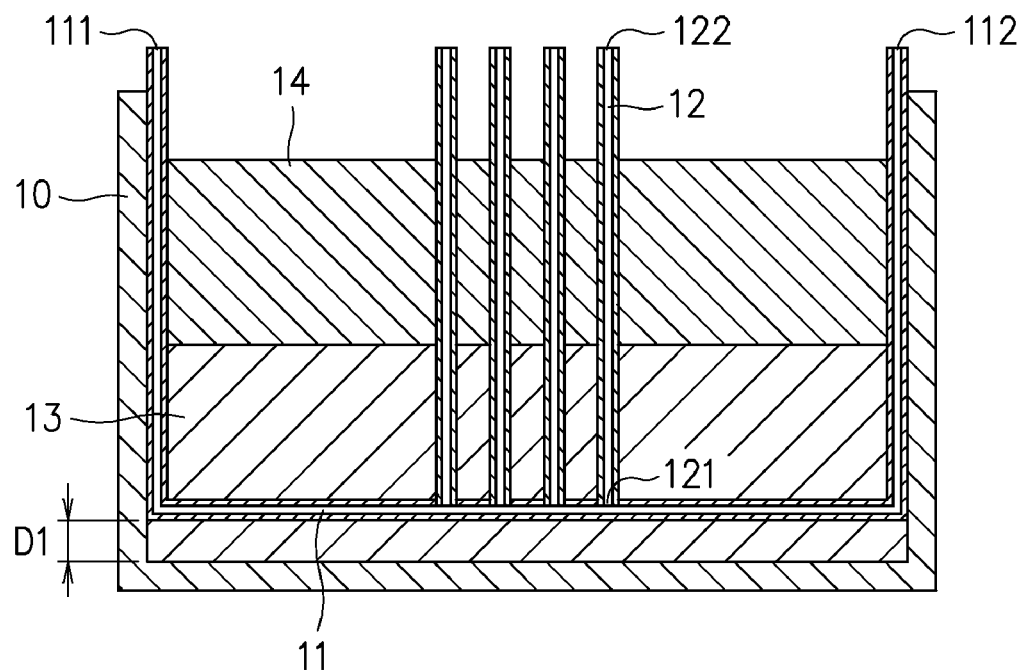

As shown in FIG. 4, the melted raw material is fed into the container 10 on top of the first solid layer 13. Similarly, after allowing the container 10 to stand for another period of time, the melted raw material of the second feeding will solidify into a second solid layer 14. It is noted that, in order to mimic different skin layers of different elasticity in real skin, the first solid layer 13 and the second solid layer 14 can be made of different mixtures of gelatin and water in different proportions. For instance, the proportion of gelatin and water in the mixture for forming the first solid layer 13 is 1:20, while the proportion of gelatin and water in the mixture for forming the second solid layer 14 is 1:15, by that it is able to form two different layers stacking in the container 10. It is noted that as the first channel 11 is spaced from the inner bottom of the container 10 by the distance D1, the first channel 11 will be completely concealed inside the first solid layer 13. Moreover, each second channel 12 is connected to the first channel 11 by the bottom 121 thereof while extending vertically upward therefrom. In this embodiment, the top 122 of each second channel 12 is exposed and extruding out of the top surface of the topmost second solid layer 14. However, ideally, each second channel 12 should be concealed by the second solid layer 14 while enabling the top 122 of each second channel 12 to be positioned at about the same level with the top surface of the second solid layer 14.

Figure 5:
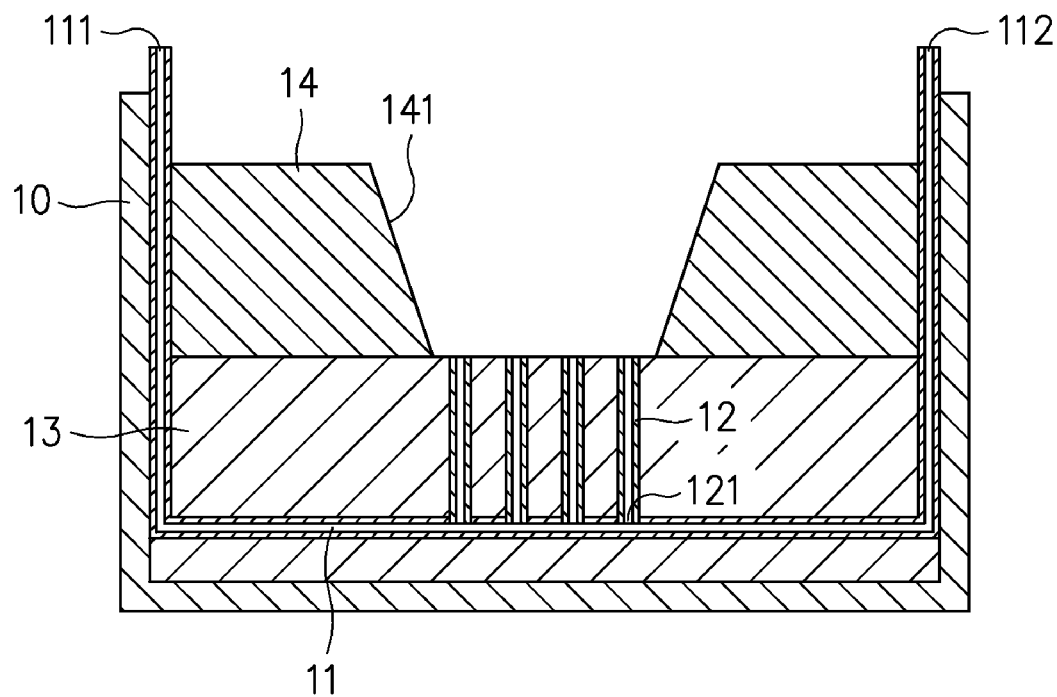
FIG. 5 is a schematic diagram showing a phantom formed with a sculpted opening simulating a wound according to an embodiment of the present invention.

As shown in FIG. 5, there is a recess 141 formed at the topmost second solid layer 14 which is connected to each second channel 12 by the bottom thereof. It is noted that the recess 141 can be formed after the formation of the second solid layer 14 or can be integrally formed with the formation of the second solid layer 14 by the use of a mold. It is noted that each of the second channel 12 can be trimmed for matching the depth of the recess 141 after the recess 141 is formed. It is noted that the amount of the second channel 12 as well as its inner diameter are dependent upon the size, shape and depth of the recess 141 as it is the sculpted opening simulating a wound.

Figure 6:
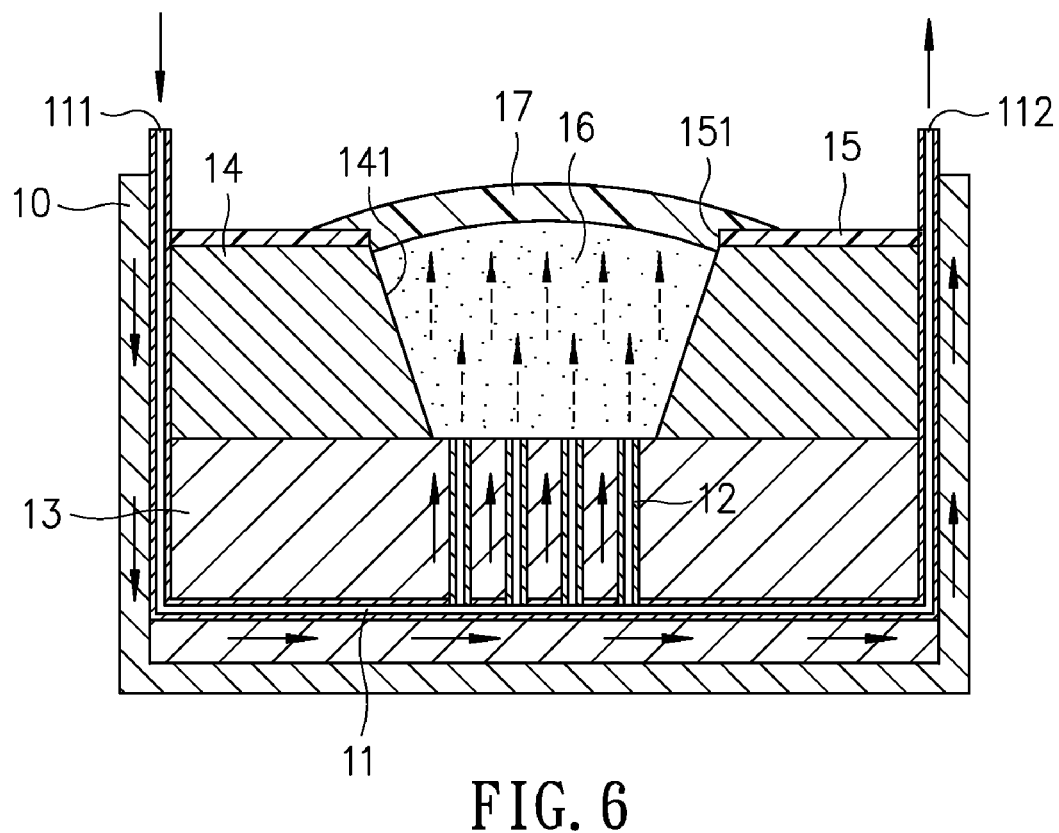
FIG. 6 is a schematic diagram showing the flowing of an exudate in a phantom of the invention.

In FIG. 6, an artificial skin 15 is covered on top of the second solid layer 14, which is configured with a hole 151 matching the size of the recess 141. Moreover, the recess 141 is filled by a dressing 16 as the dressing 16 is covered by a patch 17. It is noted that the dressing 16 is connected with a vacuum pump, a temperature sensor, a flow sensor or a pressure sensor whichever is configured in a NPWT system. The phantom of the invention is characterized in that: after an exudate is fed into the first channel 11 through the inlet 111 thereof, it can flow into those vertical second channels 12, indicating by the solid arrows, as the second channels 12 are connected to the first channel 11 by the bottom thereof, and then the exudate flowing in the second channels 12 will permeate into the dressing 16, as indicating by the dotted arrows, while the rest of the exudate is flowing out of the first channel 11 through the outlet 112 thereof. When the exudate is permeating into the dressing 16 for mimicking an actual breeding wound, the NPWT system is activate to detect the negative pressure variation with respect to the recess for analyzing how the oozing exudate can affect the negative pressure of the NPWT system. By the way, the artificial skin 15 can be integrally formed with the second solid layer 14, or can be an independent unit to be covered on top of the second solid layer 14 after the formation of the second solid layer 14.

Figures 7, 8:
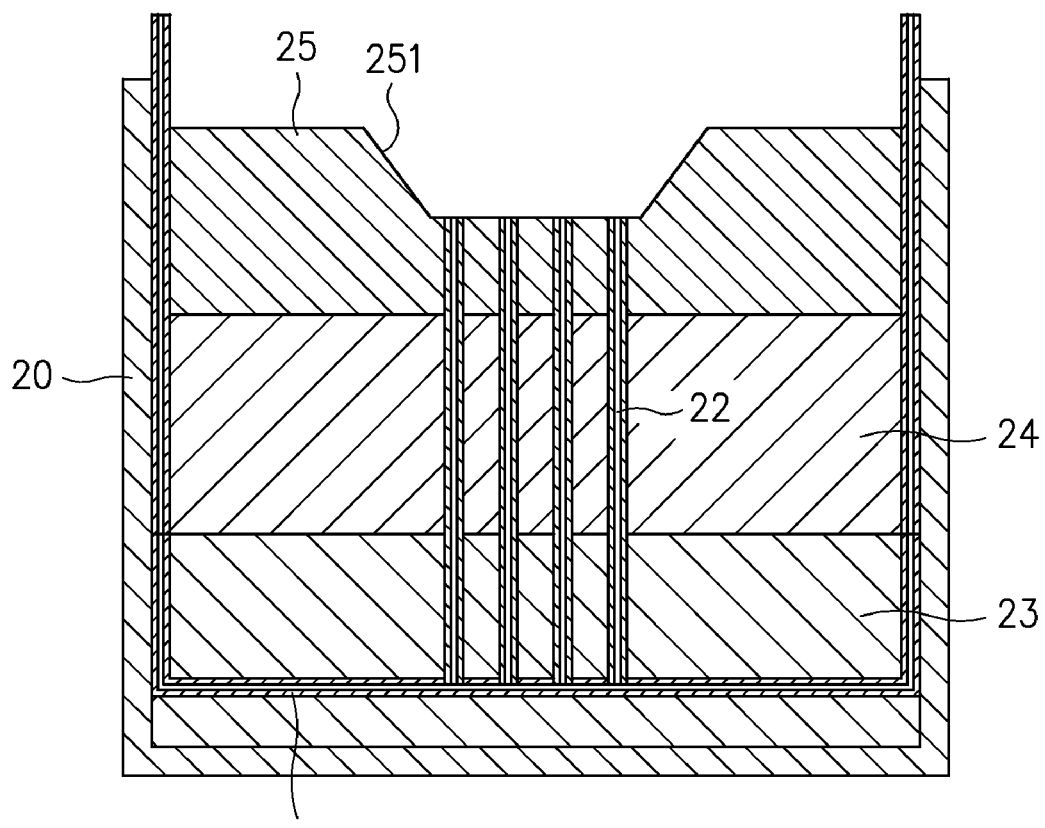
FIG. 7 is a table comparing the experiment results obtained from an actual wound on flesh and a phantom with sculpted opening simulating a wound.
FIG. 8 is a schematic diagram showing a phantom formed with a sculpted opening simulating a wound according to another embodiment of the present invention.

Please refer to FIG. 7, which is a table comparing the experiment results obtained from an actual wound on flesh and a phantom with sculpted opening simulating a wound. In this experiment, when the negative pressure is set to be −125 mmHg for an actual wound and a phantom with sculpted opening both of 30 mm in diameter that are covered by the same PU dressing, the negative pressure measured at the sculpted opening of the phantom is about the same as that measured at the actual wound, but the phantom can reach a set negative pressure faster than the actual wound. Thus, it is proving that the phantom of the invention is quite capable of mimicking an actual wound.

Please refer to FIG. 8, which is a schematic diagram showing a phantom formed with a sculpted opening simulating a wound according to another embodiment of the present invention. In FIG. 8, there are similarly a first channel 21 and several second channels 22 formed inside the container 20. But instead of two solid layer, i.e. one first solid layer 13 and one second solid layer 14 as shown in FIG. 5, there are three solid layers 23, 24, 25. It is noted that the formation of the three solid layers 23, 24, 25 is the same as the step described in FIG. 5 and is formed by repeating the feeding of the raw material and the cooling of the melted raw material. The three solid layers 23, 24, 25 are all made from mixtures of gelatin and water but in different proportions, that is, the proportion of gelatin and water in the mixture for forming the bottommost solid layer 23 is 1:20, the proportion of gelatin and water in the mixture for forming the middle solid layer 24 is 1:15, and the proportion of gelatin and water in the mixture for forming the topmost solid layer 25 is 1:10. Although there is no specific regulation defining how the proportion should be for different solid layers, it is generally that the higher the solid layer is formed in the phantom, the less the water proportion it will be. That is, the proportion of water in the mixture used for forming the bottommost solid layer 23 is higher than that for forming the topmost second solid layer 25. There is a recess 251 formed in the topmost solid layer 25, which simulates a shallow wound comparing with the recess 141 shown in FIG. 5. Nevertheless, the bottom of the recess 251 is also connected to the second channels for enabling the same to mimic a bleeding wound.

To sum up, the present invention provides a phantom suitable to be used for experimenting how exudates can affect the efficiency of a negative pressure wound therapy (NPWT) system as it is configured with an exudate network connecting to a sculpted opening simulating a breeding wound. Moreover, it can be manufactured by a simple process with less cost, so that it is used as a test platform in various experiments, e.g. the experiment for verifying the effectiveness of a NPWT system when such NPWT system is designed for treating wounds of various sizes, shapes and depths; the experiment for comparing the negative pressure variation caused by the use of different dressings in a wound; and the experiment for comparing the performance of different NPWT systems, and so on. In addition, it can be used as an specification verification platform for assisting the developing of a new NPWT system in a manner that it can shorten the time required for developing a new NPWT system since there can be less animal experiments required.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A method for manufacturing a phantom, comprising the steps of:

disposing an exudate network with interconnecting at least a first channel and at least a second channel in a container in a manner that the first channel is transversely disposed for an exudate to flow laterally in the container and the top portion of the second channel is longitudinally disposed for the exudate to flow vertically in the container;

forming a plurality of solid layers by stacking one on top of another while enabling the first channel to be disposed at the bottommost solid layer and the top of the second channel to be disposed either inside the topmost solid layer or exposed outside the top of the topmost solid layer as the bottom of the second channel is connected to the first channel and extending therefrom upward to the topmost solid layer; and forming a recess in the topmost solid layer in a manner that the bottom of the recess is connected to the second channel.

2. The phantom manufacturing method of claim 1, wherein the forming of the plural solid layers inside the container further comprises a repetitive process including the steps of:

feeding a melted raw material for forming the phantom into the container; and cooling the melted raw material so as to form at least one of the plural solid layers.

3. The phantom manufacturing method of claim 2, wherein the repetitive process includes the steps of:

feeding the melted raw material into the container to an extent that the first channel is submerged under the raw material while leaving the top of the second channel exposed;

allowing the container to stand for a period of time until the melted raw material is cooled down and thus solidified into the first solid layer;

feeding again the melted raw material into the container on top of the first solid layer; and allowing the container to stand for a period of time again until the melted raw material disposed on top of the first solid layer is cooled down and thus solidified into the second solid layer.

4. The phantom manufacturing method of claim 3, wherein after forming the first solid layer, the repetitive process further includes the step of:

feeding the melted raw material into the container into the container at an amount suitable for forming at least a solid layer so as to be used for forming at least a middle solid layer.

5. The phantom manufacturing method of claim 1, wherein the first channel is a network composed of a plurality of interconnecting flow canals.

6. The phantom manufacturing method of claim 1, wherein the first channel is a tube-like structure configured with at least an outlet and at least an inlet in a manner that the at least one inlet is provided for the exudate to flow into the first channel while the at least one outlet is provided for the exudate to flow out of the first channel.

7. The phantom manufacturing method of claim 1, wherein the second channel is a narrow straight tube-like structure being formed in a manner that the bottom of the second channel is connected to the first channel and the top thereof is extending vertically upward by a length.

8. The phantom manufacturing method of claim 1, wherein the melted raw material for forming the phantom is a material selected from the group consisting of various mixtures of gelatin and water in different proportions.

9. The phantom manufacturing method of claim 8, wherein the proportion of water in the mixture used for forming the first solid layer is higher than that for forming the second solid layer.

10. The phantom manufacturing method of claim 3, wherein during the period of time when the container is allowed to stand for the solid layer to solidify, a cooling device is used for assisting the melted raw material to cool down and thus solidify.

11. A phantom, comprising:
a plurality of solid layers, formed by stacking one on top of another while enabling a second solid layer to be disposed on top of a first solid layer in the plural solid layers; and
at least an exudate network, formed inside the plural solid layers with interconnecting at least one first channel and at least one second channel in a manner that the at least one first channel is transversely disposed for an exudate to flow laterally in the first solid layer and the at least one second channel is longitudinally disposed for the exudate to flow vertically;
wherein, the top of the second channel is disposed either at the top of the second solid layer or exposed outside the second solid layer as the bottom of the second channel is connected to the first channel and extending therefrom upward to the topmost solid layer.

12. The phantom of claim 11, wherein the first channel is a network composed of a plurality of interconnecting flow canals.

13. The phantom of claim 11, wherein the first channel is a tube-like structure configured with at least an outlet and at least an inlet in a manner that the at least one inlet is provided for the exudate to flow into the first channel while the at least one outlet is provided for the exudate to flow out of the first channel.

14. The phantom of claim 11, wherein the second channel is a narrow straight tube-like structure being formed in a manner that the bottom of the second channel is connected to the first channel and the top thereof is extending vertically upward by a length.

15. The phantom of claim 11, wherein each of the plural solid layers is formed from the cooling down and thus the solidification of a melted raw material for forming the phantom.

16. The phantom of claim 11, wherein the melted raw material for forming the phantom is a material selected from the group consisting of various mixtures of gelatin and water in different proportions.

17. The phantom of claim 16, wherein the proportion of water in the mixture used for forming the first solid layer is higher than that for forming the second solid layer.

18. The phantom of claim 15, further comprising:
a cooling device, for assisting the cooling down and the solidification of the melted raw material.

* * * * *